(12) United States Patent
Quallich et al.

(10) Patent No.: US 6,255,320 B1
(45) Date of Patent: Jul. 3, 2001

(54) POLYMORPHS OF A CRYSTALLINE AZO-BICYCLO (2,2,2) OCTAN-3-AMINE CITRATE AND THEIR PHARMACEUTICAL COMPOSITIONS

(75) Inventors: George Joseph Quallich, North Stonington, CT (US); Lewin Theophilus Wint, Wilmette, IL (US); Michael James Castaldi, Pawcatuck, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/566,307

(22) Filed: May 8, 2000

Related U.S. Application Data

(60) Provisional application No. 60/136,992, filed on Jun. 1, 1999.

(51) Int. Cl.[7] .......................... A61K 31/46; C07D 453/02
(52) U.S. Cl. ............................................. 514/305; 546/133
(58) Field of Search ............................... 514/305; 546/133

(56) References Cited

U.S. PATENT DOCUMENTS 5,939,433 * 8/1999 Ito et al. ............................... 514/305

OTHER PUBLICATIONS

Hesketh, P.J. et al. : Randomized phase II study of the Neurokinin 1 receptor antagonist CJ–11,974 in the control of Cisplatin–induced emesis. J. Clin. Oncol. vol. 17, pp. 338–343, Jan. 1999.*

Biles, J.A. : Crystallography. Part II. J. Pharm. Sci. vol. 51, pp. 601–617, Jul. 1962.*

* cited by examiner

*Primary Examiner*—Charanjit S. Aulakh
(74) *Attorney, Agent, or Firm*—Peter C. Richardson; Paul H. Ginsburg; Jolene W. Appleman

(57) ABSTRACT

A single crystalline polymorphic form (2S,3S)-N-(methoxy-5-t-butylphenylmethyl-2-diphenylmethyl-1-azobicyclo[2,2,2] octan-3-amine citrate(citrate monohydrate) and its pharmaceutical composition. The pharmaceutical composition of the polymorphic form if the citrate monohydrate has advantageous stability for formulation to treat emesis. The administration of this pharmaceutical composition is immediate release, oral dosage form preferably by tablet or capsule or intravenous.

10 Claims, No Drawings

POLYMORPHS OF A CRYSTALLINE AZO-BICYCLO (2,2,2) OCTAN-3-AMINE CITRATE AND THEIR PHARMACEUTICAL COMPOSITIONS

The application claims the benefit of U.S. Provisional Patent Application No. 60/136,992 filed Jun. 1, 1999.

BACKGROUND OF THE INVENTION

This invention is directed to an anhydrous (2S,3S)-N-(methoxy-5-t-butylphenylmethyl-2-diphenylmethyl-1-azobicyclo[2,2,2] octan-3-amine citrate monohydrate salt, its single crystalline polymorphic Form A, and pharmaceutical composition containing them. The invention is also directed to a CNS active NK-1 receptor antagonist for treating emesis in a mammal including humans. Treating is defined here as preventing and treating.

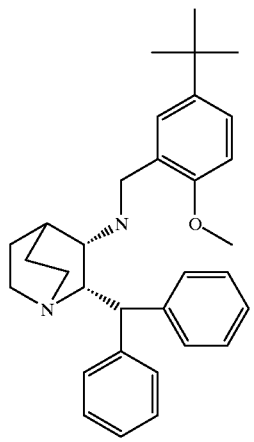

U.S. Pat. No. 5,393,762 and U.S. Ser. No. 08/816,016, both incorporated by reference, describe pharmaceutical compositions and treatment of emesis using NK-1 receptor antagonists. The citrate monohydrate has significantly enhanced stability over other salt forms such as the benzoate which was unstable even at 5° C. The mesylate form is deliquescent.

SUMMARY OF THE INVENTION

The present invention relates to the citrate monohydrate of (2S,3S)-N-(methoxy-5-t-butylphenylmethyl-2-diphenylmethyl-1-azobicyclo[2,2,2]octan-3-amine. In one embodiment of the invention, the citrate monohydrate is a crystalline stable nonhygroscopic single form. The crystalline habits are plates and are characterized by the x-ray powder detraction pattern given below:

| Citrate Monohydrate | | | | | | | |
|---|---|---|---|---|---|---|---|
| Peak No. | 1 | 2 | 3 | 4 | 5 | 6 | 7 |
| d space | 13.28 | 7.70 | 7.45 | 6.34 | 5.33 | 5.06 | 4.40 |

The crystalline citrate monohydrate salt is nonhygroscopic, and is characterized by loss of water (volatilization) at about 116° C. and a melt onset of at about 152.7° C. The anhydrous citrate was converted to the monohydrate in water.

A pharmaceutical composition having CNS active NK-1 receptor antagonist activity comprises the polymorphic Form A in an amount effective in the treatment of emesis, and a pharmaceutically acceptable carrier. A method of treating emesis comprises administering to a subject in need of treatment an emetic effective amount of the polymorphic form of the compound.

A method of making the polymorphic Form A of (2S,3S)-N-(methoxy-5-t-butylphenylmethyl-2-diphenylmethyl-1-azobicyclo 2,2,2 octan-3-amine citrate monohydrate salt comprises adding citric acid to a solution of the free base in acetone. The solid was dissolved for about two hours. The clear solution was filtered and stirred overnight. Filtered isopropyl ether was added followed by the addition of filtered water. The resulting mixture was stirred at ambient termperature until crystallization started and granulated for about 16 hours. The white crystalline form was collected by filtration and dried at about 45° C. under vacuum with a nitrogen purge for about 24 hours.

DETAILED DESCRIPTION OF THE INVENTION

A method of making crystalline citrate monohydrate, polymorphic Form A comprises the addition of 353.9 gm, 1.1 equivalents of citric acid (anhydrous, 99.5+%) to a solution of the free base, 785 gm in acetone, 7.85 liters. After dissolution of the solid for about 2 hours, clear solution was filtered, stirred overnight and filtered isopropyl ether, 7.85 liters was added followed by the addition of filtered water, 334 mls. The resulting mixture was stirred at ambient temperature until crystallization started and granulated for an additional 16 hours. The white crystalline salt formed was collected by filtration and dried at 45° C. under vacuum with a nitrogen purge for 24 hours to provide 992 gm, (89.9% yield). The resulting citrate monohydrate salt, polymorphic form was characterized via PLM, X-ray powder diffraction, proton NMR, Karl Fisher, DSC and elemental analysis. X-ray powder diffraction and PLM revealed it to be crystalline. The crystalline habit encountered were plates. The most intense reflections, d spacings, observed by X-ray powder diffraction were 13.280, 7.702, 7.446, 6.337, 5.332, 5.057, and 4.398 Å. The crystals exhibited a loss of water (volatilization) at 116° C. and a melt onset of 152.7 ° C. with decomposition. Hygroscopicity measurements demonstrated that 2.52% wt./wt. water was absorbed at 90% RH. Karl Fisher analysis showed the presence of 2.7% water (2.66% theoretical) verifying that the monohydrate was synthesized. Elemental analysis validated the purity of the salt synthesized.

Slurrying the anhydrous citrate in water yields the crystalline monohydrate that does not lose its water under drying conditions, e.g., at 45° C. in vacuo.

The effective dosage for the pharmaceutical composition of the citrate monohydrate depends on the intended route of administration, the indicator, the indication to be treated, and other factors such as age and weight of the subject. In the following dosage ranges, the terms "mg A" refers to milligrams of the monohydrate. A recommended range for oral dosing is 5–300 mgA/day, preferably 40–200 mgA/day more preferably 40–80 mgA/day, in single or divided doses. A recommended range for oral administration in oral forms such as pills or tablets is 2.5 mgA/day to 160 mgA/day and preferably 5–80 mgA/day. It can also be given by intravenous.

The following examples illustrate the methods and compounds of the present invention. It will be understood, however, that the invention is not limited to the specific Examples.

EXAMPLE 1

Preparation of the Crystalline Citrate Monohydrate,

A 47 gram portion of the free base was suspended in 470 milliliters of isopropyl ether under ambient conditions. To the resulting thin white slurry, 21.42 grams of anhydrous citric acid was added at room the temperature. This slurry was then used for the conversion to the monohydrate by suspending in 150 mls water for 18 hours. The slurry was filtered to give a white crystalline solid. An x-ray configuration was obtained confirming that the compound is citrate monohydrate.

What is claimed is:

1. A crystalline forms of (2S,3S)-N-(methoxy-5t-butylphenylmethyl-2-diphenylmethyl-1-azobicyclo[2,2,2]octan-3-amine citrate having the formula

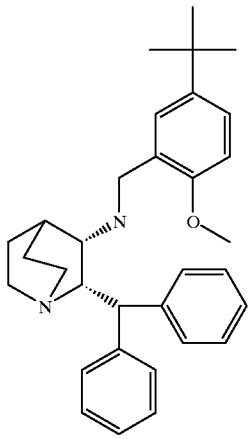

wherein said crystalline form is a stable polymorphic Form A exhibiting the X-ray powder diffraction pattern

| Peak No. | 1 | 2 | 3 | 4 | 5 | 6 | 7 |
|---|---|---|---|---|---|---|---|
| d space. | 13.28 | 7.70 | 7.45 | 6.34 | 5.33 | 5.06 | 4.40 |

2. The citrate monohydrate polymorphic form according to claim 1 wherein its crystalline habits are plates.

3. The citrate monohydrate polymorphic form according to claim 1 wherein the citrate monohydrate is nonhygroscopic.

4. The citrate monohydrate polymorphic form according to claim 1 wherein volatilization occurs at about 116° C.

5. The citrate monohydrate polymorph according to claim 1 wherein melt onset occurs at about 152.7° C.

6. A pharmaceutical composition having CNS active NK-1 receptor antagonist activity comprising the polymorphic Form according to claim 1, in an amount effective in the treatment of emesis, and a pharmaceutically acceptable carrier.

7. A method of treating emesis which comprises administering to a subject in need of treatment an antiemetic effective amount of the polymorphic Form A of the compound of claim 1.

8. A method of making the crystalline polymorphic Form of (2S,3S)-N-(methoxy-5-t-butylphenylmethyl-2-diphenylmethyl-1-azobicyclo2,2,2 octan-3-amine citrate monohydrate salt comprising:

Adding citric acid to a solution of the free base, in acetone; dissolving the solid for about 2 hours; filtering and stirring the clear solution overnight; Adding filtered isopropyl ether followed by the addition of filtered water; Stirring the resulting mixture at ambient temperature until crystallization starts and granulating for an about 16 hours; and collecting the white crystalline salt formed by filtration and drying at about 45° C. under vacuum with a nitrogen purge for about 24 hours.

9. The method of claim 8 wherein the slurrying is carried out under ambient conditions for about 1.5 to 72 hours granulation in isopropyl ether, isopropyl alcohol and water.

10. The method of claim 8 wherein the citric acid is greater than 99.5% anhydrous.

* * * * *